United States Patent [19]

Konishi

[11] Patent Number: 4,637,996

[45] Date of Patent: Jan. 20, 1987

[54] ANTIULCER COMPOSITION CONTAINING A DIPEPTIDE COMPOUND

[75] Inventor: Jin-emon Konishi, Musashino, Japan

[73] Assignee: Nippon Zoki Pharmaceutical Co., Ltd., Osaka, Japan

[21] Appl. No.: 737,420

[22] Filed: May 24, 1985

[30] Foreign Application Priority Data

May 24, 1984 [JP] Japan .................................. 59-105098

[51] Int. Cl.$^4$ .............................................. A61K 37/43
[52] U.S. Cl. ......................................... 514/11; 514/19
[58] Field of Search ..................................... 514/19, 11

[56] References Cited

U.S. PATENT DOCUMENTS 3,965,260  6/1976  McArthur et al. .................... 514/19
4,127,535 11/1978  Coy et al. .............................. 514/19

OTHER PUBLICATIONS

Analytical Chemistry, vol. 50, No. 8 (1978), 1180–1184.
Journal of Chromatography, 240, (1982), 206–208.

Primary Examiner—Delbert R. Phillips
Attorney, Agent, or Firm—Birch, Stewart, Kolasch & Birch

[57] ABSTRACT

An antiulcer composition containing a dipeptide or a pharmaceutically acceptable salt thereof as an active ingredient. The dipeptide employed can be any combination of two amino acids selected from glycine (Gly), serine (Ser), histidine (His) and lysine (Lys) or pharmaceutically acceptable salts or metal complexes thereof. The preferred dipeptide active substances are Gly-Ser, Ser-His, His-Lys or cyclic His-Lys.

5 Claims, No Drawings

ANTIULCER COMPOSITION CONTAINING A DIPEPTIDE COMPOUND

DETAILED DESCRIPTION OF THE INVENTION

The present invention is concerned with an antiulcer composition containing a dipeptide or pharmaceutically acceptable salt thereof as an active ingredient.

Recently various kinds of peptides and their derivatives have been synthesized, and their pharmaceutical effects on the organism have been investigated. After intensive investigation of physiological activities of various peptide compounds, the inventor has found that the dipeptide of the present invention has an excellent antiulcer effect, and has thus accomplished this invention.

The dipeptide of this invention has been known, but its physiological functions have not been described.

An object of the present invention is to provide an excellent antiulcer composition containing at least one of such dipeptides or a pharmaceutically acceptable salt thereof as an active ingredient.

The dipeptide of the present invention can be any combination of two amino acids selected from glycine (Gly), serine (Ser), histidine (His) and lysine (Lys). The pharmaceutical composition of the present invention contains at least one of the dipeptides, pharmaceutically acceptable salts or metal complexes thereof.

The preferred dipeptide in the present antiulcer composition is the dipeptide with Gly, Ser or His at the amino terminal and Ser, His or Lys at the carboxyl terminal, e.g. Gly-Ser, Ser-His or His-Lys. Also the dipeptide in this composition may include a cyclic dipeptide, preferably cyclic His-Lys ( His-Lys ).

The amino acid residues in the invention can be any combination of the D-isomer and L-isomer.

The dipeptide of the present invention can be synthesized in the solid phase, the liquid phase or enzymatically. Further, the dipeptide can also be obtained from natural products by extraction.

When formulated as drugs, the dipeptide of the invention can be used in the form of a pharmaceutically acceptable salt; a salt with an inorganic acid such as hydrochloric acid, sulfuric acid, nitric acid, hydrobromic acid, phosphoric acid, perchloric acid, thiocyanic acid or boric acid; a salt with an organic acid such as formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, oxalic acid, maleic acid, p-toluenesulfonic acid, naphthalenesulfonic acid or sulfanilic acid; or a salt with an alkali metal such as lithium, sodium or potassium, an alkaline-earth metal such as calcium or magnesium, and other metals such as aluminum.

In addition, the dipeptide includes its metal complex, for example, complexes with zinc, nickel, cobalt, copper, iron etc. The salts and metal complexes of this dipeptide can be produced from the free dipeptide and/or converted to another salt or metal complex in the usual way.

The pharmacological effects of the dipeptide of the present invention are described below.

ACUTE TOXICITY

The dipeptide of the invention was intravenously administered to mice and the acute toxicity was evaluated from the number of the dead animals after 72 hours.

As the result, the $LD_{50}$ of the dipeptide of the present invention were all higher than 2,000 mg/kg.

INHIBITION OF HISTAMINE-INDUCED ULCER FORMATION

The drugs were intravenously administered (i.v.) to groups of 10 Wister strain rats weighing 180 to 210 g which had been starved for 24 hours. Immediately thereafter, 300 mg/kg of histamine dihydrochloride was administered intraperitoneally (i.p.) F. Bürcher et al; [Beith. Path. Anat., 81, 391 (1928)]. Four hours later, each animal was bled to death by decapitation, and the stomach was removed. 7.5 ml of physiological saline was infused into the removed stomach and partially fixed in 10% formalin for 10 minutes. Then, the stomach was incised along the greater curvature. The sum of the surface area of the ulcer lesion on the glandular part of the stomach was designated as the ulcer coefficient.

The results are given in Table 1.

TABLE 1

| Test Drug | Dosage (mg/kg) | Ulcer coefficient[d] | Inhibition rate (%) |
|---|---|---|---|
| None | 2.5 ml/kg[a] | 45.0 ± 12.1 | — |
| Gly—Ser | 20 | 6.0 ± 4.3 | 86.6 |
| Gly—Ser | 50[c] | 18.6 ± 7.3 | 58.6 |
| Ser—His | 20 | 17.1 ± 8.5 | 62.1 |
| His—Lys | 20 | 14.8 ± 8.9 | 67.2 |
| ⌐His — lys⌐ [b] | 20 | 14.9 ± 6.0 | 66.8 |
| Cimetidine | 20 | 19.1 ± 10.6 | 57.6 |

[a] physiological saline
[b] cyclic histidyllysine
[c] oral administration
[d] mean ± S.E.

As clearly seen in Table 1, the dipeptide of the present invention has a significant antiulcer effect. Thus, the dipeptide is useful as a preventive medicine or remedy for ulcers of peptic organs such as the stomach and duodenum, aphthous stomatitis, scalds, burns, etc.

The dipeptide of the invention, which can be easily synthesized, has low toxicity and fewer side effects, and therefore is very useful as a medicine.

The dipeptide of the present invention can be formulated into a pharmaceutical compositon by combination with an appropriate carrier or diluent, and into preparations in solid, semisolid or liquid form in the usual ways for oral or parenteral administration.

In pharmaceutical dosage form, the dipeptide can be used in the form of a pharmaceutically acceptable salt or metal complex, and also can be used alone or in combination with other pharmaceutically active compounds.

In case of oral preparation, the dipeptide of the invention can be used alone or combined with an appropriate additive to make a tablet, powder, granule or capsule, e.g. with conventional additives such as lactose, mannitol, corn starch or potato starch; with binders such as crystalline cellulose, cellulose derivatives, acacia, corn starch or gelatin; with disintegrators such as corn starch, potato starch or sodium carboxymethylcellulose; with lubricants such as talc or magnesium stearate; and if desired, with a diluent, buffering agent, moistening agent, preservative and flavor.

Further, the dipeptide can be encapsulated into liposome prepared from a suitable liquid, for example a phospholipid such as lecithin, sphingomyelin, phosphatidylethanolamine, phosphatidylserine, cholesterol, phosphatidic acid, diethyl phosphate, stearylamine etc. to make suitable preparations. The liposome can be either of a multi-layer or mono-layer structure, and can also encapsulate a stabilizer, buffering agnet, etc. Furthermore, the liposome can be made into capsule form.

For parenteral administration, the dipeptide of the invention can be formulated into preparations for injection by dissolving, suspending or emulsifying in an aqueous or non-aqueous solvent, such as distilled water for injection, physiological saline, Ringer's solution, vegetable oil, synthetic aliphatic acid glyceride, esters of higher aliphatic acid or propylene glycol, and can contain a preservative, stabilizer, buffering agent or solubilizer when necessary. Further, the dipeptide can be presented as a dry powder for injection by dissolving in a liquid immediately before use, or as a suppository, ointment, etc. by mixing with suitable bases.

The desirable dose of the dipeptide of the present invention varies with the subject, form of the drug, method and period of administration. The recommended oral dosage for an adult is 1 to 2000 mg, preferably 20 to 1200 mg. As for parenteral administration e.g. injections, one tenth to one third of the oral dose is recommended daily.

Shown below are prescription examples which contain the dipeptide of the invention as an active ingredient.

| Prescription example 1 (injection) | |
|---|---|
| Component | Content in an ampule (mg) |
| dipeptide of the invention | 10 |
| distilled water for injection | proper amount |
| sodium chloride | proper amount |
| Total | 1 ml |

| Prescription example 2 (tablet) | |
|---|---|
| Component | Content in a tablet (mg) |
| dipeptide of the invention | 50 |
| lactose | 190 |
| crystalline cellulose | 50 |
| magnesium stearate | 10 |
| Total | 300 mg |

| Prescription example 3 (capsule) | |
|---|---|
| Component | Content in a capsule (mg) |
| dipeptide of the invention | 50 |
| lactose | 250 |
| Total | 300 mg |

What we claim is:

1. A method for the treatment of ulcers in mammals which comprises administering to such a mammal an effective amount of a dipeptide as the active substance selected from the group consisting of Gly-Ser, Ser-His, His-Lys and cyclic His-Lys, or a pharmaceutically acceptable salt thereof.

2. The method of claim 1, wherein the active substance is Gly-Ser or a pharmaceutically acceptable salt thereof.

3. The method of claim 1, wherein the active substance is Ser-His or a pharmaceutically acceptable salt thereof.

4. The method of claim 1, wherein the active substance is His-Lys or a pharmaceutically acceptable salt thereof.

5. The method of claim 1, wherein the active substance is cyclic His-Lys or a pharmaceutically acceptable salt thereof.

* * * * *